(12) United States Patent
Park et al.

(10) Patent No.: US 12,194,270 B2
(45) Date of Patent: Jan. 14, 2025

(54) PRECISION ROLLER CLAMP ASSEMBLY

(71) Applicant: CareFusion 303, Inc., San Diego, CA (US)

(72) Inventors: Soon Park, Cypress, CA (US); Siddarth K. Shevgoor, Mission Viejo, CA (US)

(73) Assignee: CareFusion 303, Inc., San Diego, CA (US)

( * ) Notice: Subject to any disclaimer, the term of this patent is extended or adjusted under 35 U.S.C. 154(b) by 272 days.

(21) Appl. No.: 17/977,592

(22) Filed: Oct. 31, 2022

(65) Prior Publication Data

US 2023/0046398 A1 Feb. 16, 2023

Related U.S. Application Data

(63) Continuation of application No. 16/572,373, filed on Sep. 16, 2019, now Pat. No. 11,517,735.

(51) Int. Cl.
*A61M 39/28* (2006.01)
*A61M 5/14* (2006.01)
*A61M 5/168* (2006.01)

(52) U.S. Cl.
CPC ........ *A61M 39/286* (2013.01); *A61M 5/1411* (2013.01); *A61M 5/16813* (2013.01); *A61M 5/16881* (2013.01); *A61M 39/281* (2013.01); *A61M 2205/33* (2013.01)

(58) Field of Classification Search
CPC ........ A61M 2205/3337; A61M 39/286; A61M 39/287; A61M 5/16813; A61M 5/16881; A61M 39/285
See application file for complete search history.

(56) References Cited

U.S. PATENT DOCUMENTS

| 3,374,509 A | 9/1968 | Logan et al. |
| 4,285,492 A | 8/1981 | Bujan |
| 6,117,115 A | 9/2000 | Hill et al. |

(Continued)

FOREIGN PATENT DOCUMENTS

| DE | 3631411 A1 | 3/1988 |
| JP | S47001540 A | 1/1972 |

(Continued)

OTHER PUBLICATIONS

International Search Report and Written Opinion for Application No. PCT/US2020/050555, dated Dec. 17, 2020, 14 pages.

(Continued)

*Primary Examiner* — Deanna K Hall
(74) *Attorney, Agent, or Firm* — Morgan, Lewis & Bockius LLP

(57) ABSTRACT

A roller clamp assembly for adjusting the fluid flow rate in a flexible infusion tube is provided. The roller clamp assembly includes a housing to receive the flexible tube, a plate slideably engaged with the housing and configured to rapidly compress the flexible tube to provide a coarse fluid flow adjustment, and a roller wheel moveable engaged with the housing and configured to provide a gradual fluid flow adjustment. The plate may be a slide plate received by grooves in an exterior wall of the housing, where the plate moves orthogonally to the flexible tube, or the plate may be a shim plate that moves along an interior wall of the housing in parallel to the flexible tube. Infusion sets and methods of adjusting fluid flow rates are also provided.

20 Claims, 14 Drawing Sheets

(56) References Cited

U.S. PATENT DOCUMENTS

| | | |
|---|---|---|
| 8,313,081 B2 | 11/2012 | Adelberg |
| 2007/0090313 A1 | 4/2007 | Reynolds |
| 2009/0312719 A1 | 12/2009 | Chew |

FOREIGN PATENT DOCUMENTS

| | | |
|---|---|---|
| JP | S54075091 U | 5/1979 |
| JP | 2004033545 A | 2/2004 |

OTHER PUBLICATIONS

Japanese Office Action for Application No. 2022-516651, dated Apr. 23, 2024, 7 pages.
Japanese Office Action for Application No. 2022-516651, dated Aug. 20, 2024, 4 pages including translation.

PRECISION ROLLER CLAMP ASSEMBLY

CROSS-REFERENCE TO RELATED APPLICATIONS

This application is a continuation of U.S. patent application Ser. No. 16/572,373, entitled "PRECISION ROLLER CLAMP," filed on Sep. 16, 2019, issued as U.S. Pat. No. 11,517,735 on Dec. 26, 2022, the entirety of which is incorporated herein by reference.

TECHNICAL FIELD

The present disclosure generally relates to a gravity intravenous (IV) set or infusion pump flow control device, and in particular a precision roller clamp assembly.

BACKGROUND

Flow controllers in the form of roller clamps are used in the medical field for intravenous (IV) applications. Typical roller clamps control a flow rate through an IV tube by clamping the tube in between a roller wheel and a housing. This approach, for one, provides a limited range of flow rate control because the roller wheel is essentially too sensitive in that a small movement of the roller wheel or dimension change causes a large change in flow rate of the fluid through the tube. Thus, the relatively course flow rate change provided by a typical roller clamp makes it difficult to provide precise flow control.

Also, typical roller clamps have flow rate drifting issues based on slippage of the roller wheel, such as when fluid pressure in the tube causes the roller wheel to roll back from the adjusted position. Further, typical roller clamps are sized for a specific IV set tube dimension, which requires having different sized roller clamps for use with various IV set tube dimensions.

Thus, it is desirable to provide a precision roller wheel assembly that works with multiple IV tube sizes, provides quick course flow rate adjustments and fine flow rate adjustments, and eliminates or minimizes roller wheel slippage.

SUMMARY

One or more embodiments provide a roller clamp assembly. The roller clamp assembly includes a housing configured to receive a flexible tube. The housing includes two opposing side walls, a front wall disposed at one end of the side walls and a guide wall disposed between the side walls. The roller clamp assembly also includes a roller wheel movably disposed in the housing, the roller wheel configured to move along a longitudinal axis of the housing, wherein spacing between the guide wall and the roller wheel decreases over a length of the guide wall. The roller clamp assembly further includes a plate configured to slideably engage with a portion of the housing. The plate includes a grip member and a tube engagement member configured to compress the flexible tube a varying amount as the plate is moved in relation to the housing.

One or more embodiments provide an infusion set including an infusion component, a flexible tube and a roller clamp assembly. The roller clamp assembly includes a housing configured to receive a flexible tube. The housing includes two opposing side walls, a front wall disposed at one end of the side walls and a guide wall disposed between the side walls. The roller clamp assembly also includes a roller wheel movably disposed in the housing, the roller wheel configured to move along a longitudinal axis of the housing, wherein spacing between the guide wall and the roller wheel decreases over a length of the guide wall. The roller clamp assembly further includes a plate configured to slideably engage with a portion of the housing. The plate includes a grip member and a tube engagement member configured to compress the flexible tube a varying amount as the plate is moved in relation to the housing. An increased impingement of the roller wheel on the flexible tube is configured to reduce a fluid flow rate through the flexible tube.

One or more embodiments provide a method of adjusting a fluid flow rate through a flexible tube coupled to a fluid source. The method includes inserting the flexible tube through a roller clamp assembly comprising a housing configured to receive a flexible tube, the housing including two opposing side walls, a front wall disposed at one end of the side walls and a guide wall disposed between the side walls, a roller wheel movably disposed in the housing, the roller wheel configured to move along a longitudinal axis of the housing, wherein spacing between the guide wall and the roller wheel decreases over a length of the guide wall, and a plate configured to slideably engage with a portion of the housing, the plate including a grip member and a tube engagement member configured to compress the flexible tube a varying amount as the plate is moved in relation to the housing. The method also includes sliding the plate relative to the housing to compress the flexible tubing with a first impingement to produce a coarse adjustment that causes a rapid decrease in the fluid flow rate through the flexible tube. The method further includes rolling the roller wheel relative to the housing to compress the flexible tubing with a second impingement to produce a fine adjustment that causes a further gradual decrease in the fluid flow rate through the flexible tube.

The foregoing and other features, aspects and advantages of the disclosed embodiments will become more apparent from the following detailed description and accompanying drawings.

BRIEF DESCRIPTION OF THE DRAWINGS

The accompanying drawings, which are included to provide further understanding of the disclosure and are incorporated in and constitute a part of this specification, illustrate embodiments of the disclosure and together with the description serve to explain the principles of the disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1:
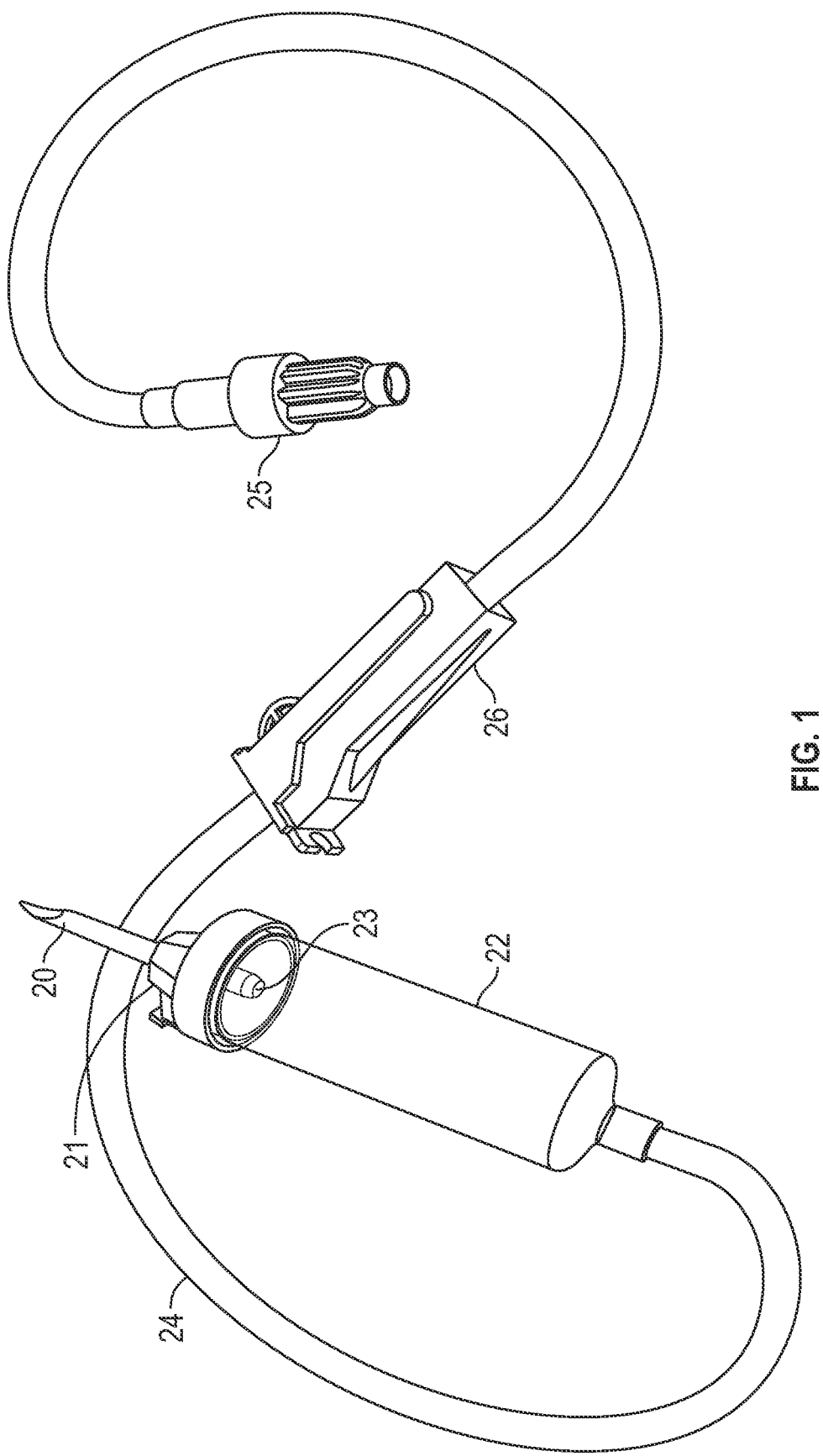
FIG. 1 depicts a perspective view of an example infusion set having a typical roller clamp.

The present disclosure relates to a roller clamp and in particular to a roller clamp for use in gravity infusion. The roller clamp regulates the flow rate of a medical fluid (for example a solution of a drug to be administered to a patient, or blood) flowing through a tube. Typically, a standard infusion set is used to infuse the fluid. An example of a standard infusion set is shown in FIG. 1.

The infusion set includes a piercing spike 20 which may either be a sharp spike for piercing rubber stoppers or rounded and blunt for insertion into a bag. The spike contains one channel for fluid and optionally a second channel for venting. A vent 21 is usually present in the vicinity of the piercing spike to allow air to flow into the drop chamber 22. The vent 21 may be provided with a bacterial filter to prevent bacteria from entering the equipment.

The drop chamber 22 has a drop generator 23 at the top of the drop chamber 22 that produces drops of a certain size. Drops from the drop generator 23 fall into the drop chamber 22 such that the drop chamber 22 is partially filled with liquid. This prevents air bubbles from entering the connector tube 24, which would be harmful to a patient. A particle filter may be provided at the lower aperture of the drop chamber 22.

The connector tube 24 connects the drop chamber 22 with the patient. The connector tube 24 is usually around 150 cm long and can be manufactured from PVC. The tube 24 is shown shortened in FIG. 1 for clarity. The connector tube 24 typically has a continuous diameter throughout the length of the tube.

At the end of the connector tube 24 is a Luer fitting 25 which is standardized for connection to all other pieces of apparatus having a standard Luer cone. The person skilled in the art will appreciate that the Luer fitting 25 can be fitted to a hypodermic needle (not shown) for infusing the medical fluid into the circulatory system of a patient (e.g., into a vein).

Between the drop chamber 22 and the Luer fitting 25 and engaging with the connector tube 24, is a roller clamp 26. The present disclosure is concerned with an improved roller clamp assembly, but a typical roller clamp 26 as known in the art will now be described for background information.

Figure 2:
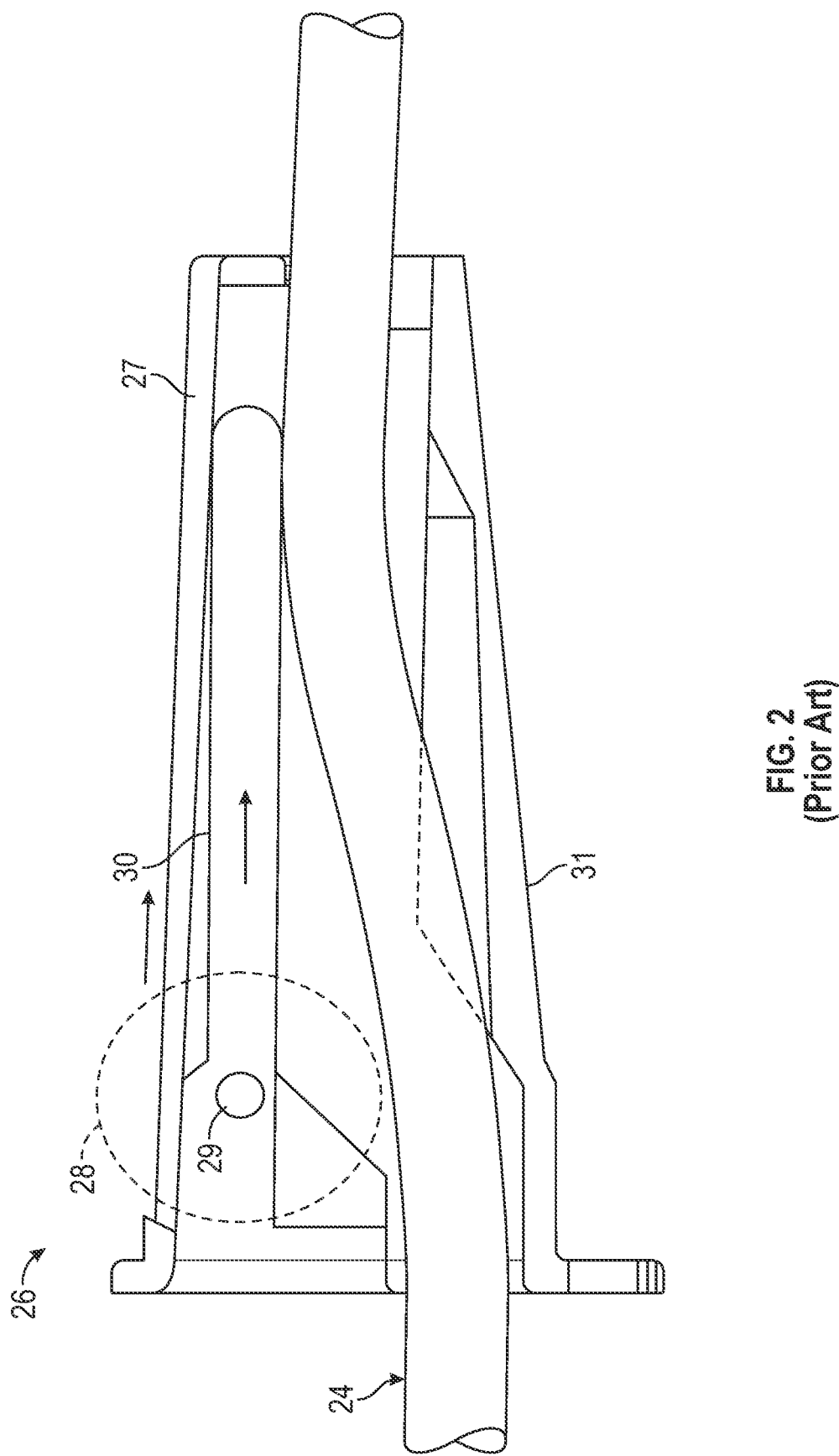
FIG. 2 depicts a cross-section side view of the roller clamp of FIG. 1.
Figure 3:
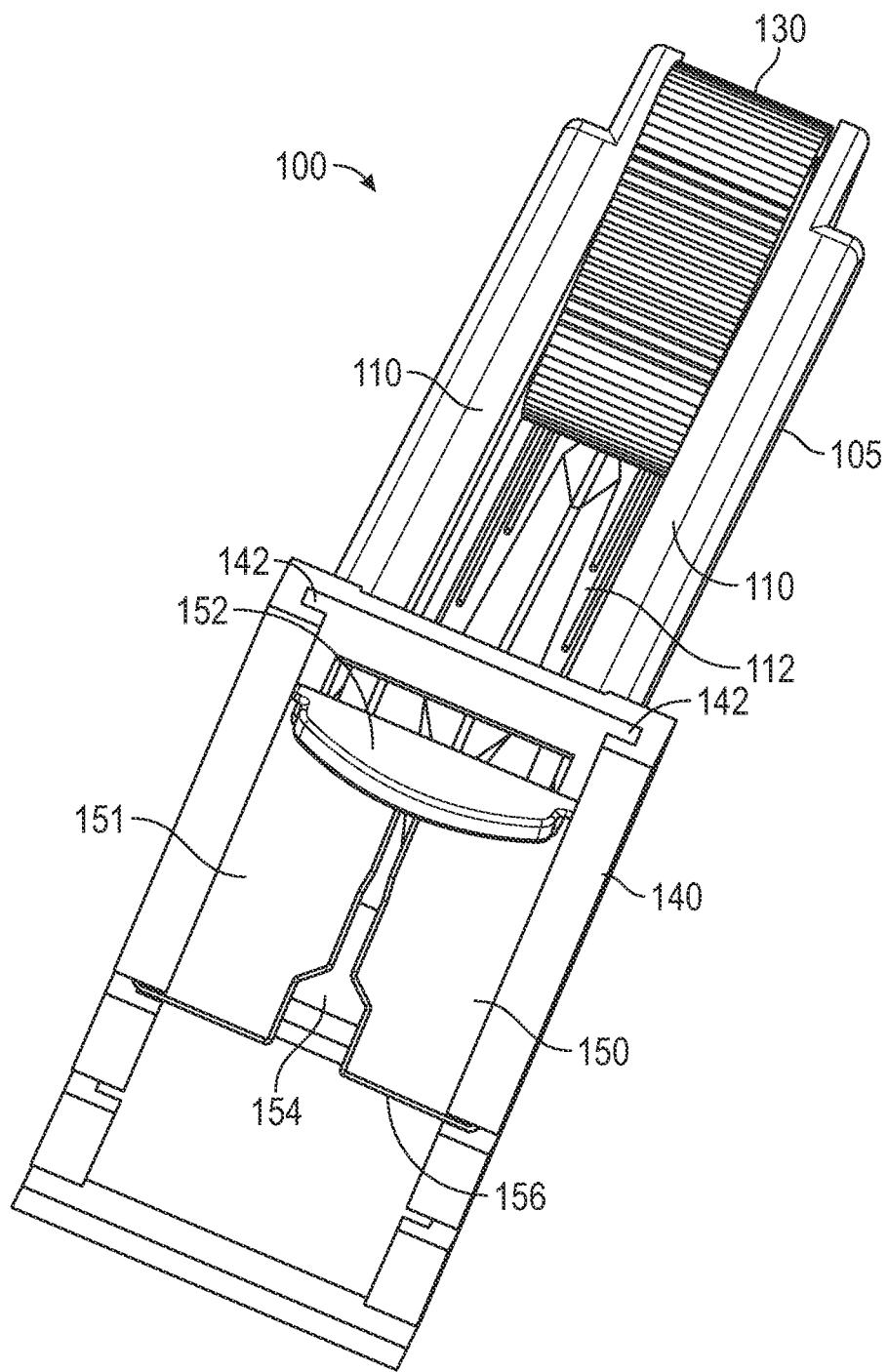
FIG. 3 depicts a perspective view of a precision roller clamp assembly.
Figure 4:
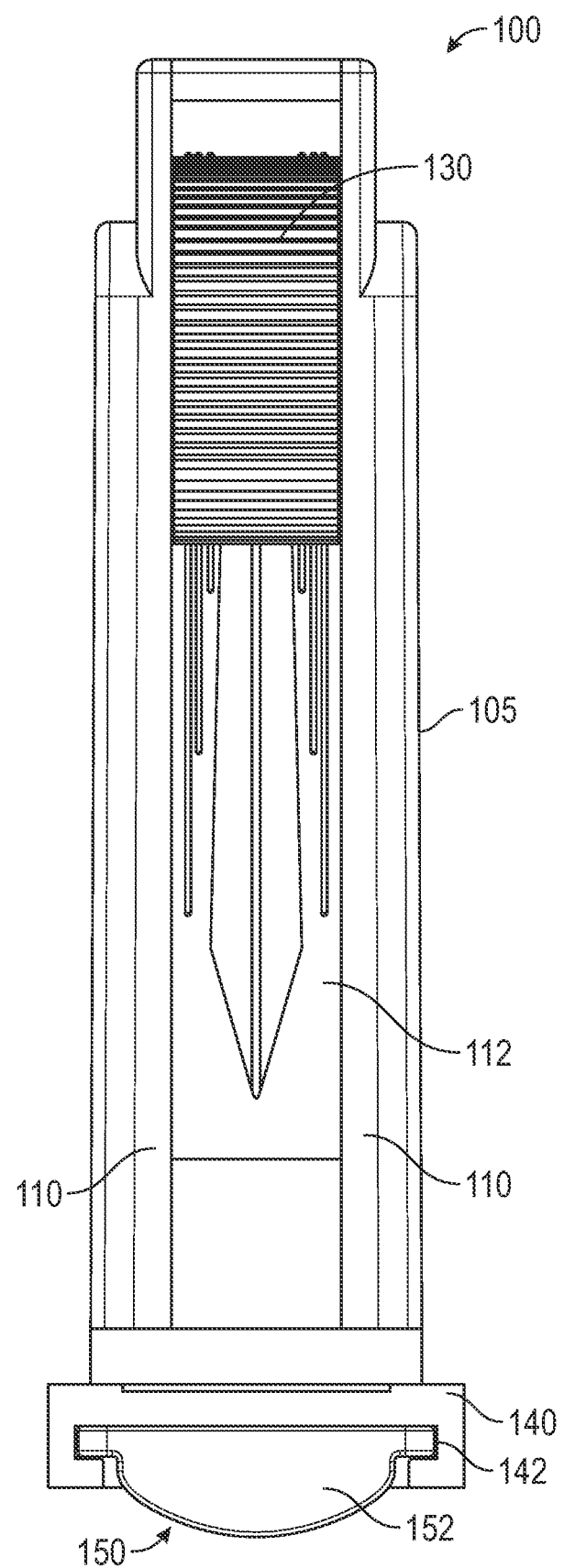
FIG. 4 depicts a top plan view of the precision roller clamp assembly of FIG. 3.

The roller clamp 26 illustrated in FIG. 2 has two opposing side walls 27 having a pair of guide grooves 30 that are aligned with each other and face each other. A flow-regulating roller 28 is provided having axially-projecting shafts 29 protruding from the centers of each side of the roller 28. The roller 28 is shown in outline for clarity. The shafts 29 of the roller 28 are captured by and seated in the guide grooves 30 so that the roller 28 can move up and down the guide grooves 30 as indicated by the arrows in FIG. 2.

The entire roller clamp 26 has four walls (see FIG. 1) in an open-ended boxlike construction and is dimensioned and configured to receive the connector tube 24. In use, the tube 24 passes through the roller clamp 26, between the two opposing side walls 27, the roller 28 and a guide wall 31 that is opposed to the roller 28.

In the roller clamp 26, the surface of the guide wall 31 converges along its length toward the position of the guide grooves 30 in the downward direction of the guide grooves 30 (e.g., in the direction of the arrows in FIG. 2). This tends to urge the connector tube 24 within the roller clamp 26 toward the guide grooves 30 and thus toward roller 28.

Thus, rolling the roller 28 downwardly along the guide grooves 30 in the direction of the gradually closer guide wall 31 in the direction of the arrows causes the roller 28 to impinge against the connector tube 24. As the roller 28 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

Thus, the roller clamp 26 controls the flow rate through the infusion tube 24 by clamping the infusion tube 24 between the roller 28 and the guide wall 31. As discussed above, this provides for a course flow rate change because a small movement of the roller 28 causes a large change in the flow rate of the fluid through the tube 24. Also, the force of the fluid in the tube 24 exerts a biasing force against the roller 28, which often leads to slippage of the roller 28 (e.g., the roller 28 rolls back) from the adjusted position. In addition, the roller 28 needs to be sized for the tube 24 dimensions, so if a different size (e.g., diameter) tubing is used, a different size roller must then be used as well.

With reference to FIGS. 3-7, a multistage precision roller clamp assembly 100 is shown. The roller clamp assembly 100 has a housing 105 having an open-ended boxlike construction and is dimensioned and configured to receive tubing, such as connector tube 24. Two opposing side walls 110 each have a guide groove 120 that are aligned with each other and face each other. A flow-regulating roller 130 is provided having axially-projecting shafts 132 protruding from the centers of each side of the roller 130. The shafts 132 of the roller 130 are seated in the guide grooves 120 so that the roller 130 can move up and down the guide grooves 120. A guide wall 112 is opposed to the roller 130 and the surface of the guide wall 112 converges along its length toward the position of the guide grooves 120.

In use, the tube 24 passes through the roller clamp assembly 100, between the two opposing side walls 110, the roller 130 and the guide wall 112 that is opposed to the roller 130. Rolling the roller 130 downwardly along the guide grooves 120 in the direction of the gradually closer guide wall 112 causes the roller 130 to impinge against the tube 24. As the roller 130 impinges on the tube 24, the tube 24 becomes squeezed, as it is a flexible material such as PVC, and the lumen of the infusion tube 24 therefore becomes smaller. In this way, by narrowing of the lumen, the flow rate of liquid passing through the connector tube 24 can be regulated.

However, regulation of the fluid flow rate by adjusting the roller 130 may provide a large change in flow rate for a small movement of the roller 130. For example, with the roller 130 in a wide open position where the roller 130 does not impinge on the tube 24, a fluid flow rate may be anywhere from 2,000 to 8,000 milliliters per hour (ml/hr). This flow rate may be too fast to count drips in a drip chamber (e.g., drop chamber 22) as the maximum flow rate for counting drops may be 250 ml/hr. Thus, for flow rates above 250 ml/hr, the roller 130 may have difficulty precisely controlling or adjusting the flow rate.

Accordingly, the precision roller clamp assembly 100 also includes a front wall 140 disposed at one end of the side walls 110. The front wall 140 includes grooves 142 configured to receive a slide plate 150. The slide plate 150 includes a plate wall 151, a grip member 152 and a tube engagement channel 154. The grip member 152 may protrude out (e.g., project orthogonally) from the plate wall 151 and provide a surface that may be pushed or pulled to slidably move the slide plate 150 within the grooves 142, the slide plate 150 being movable towards or away from the tube 24 disposed through the roller clamp assembly 100.

Figure 5:
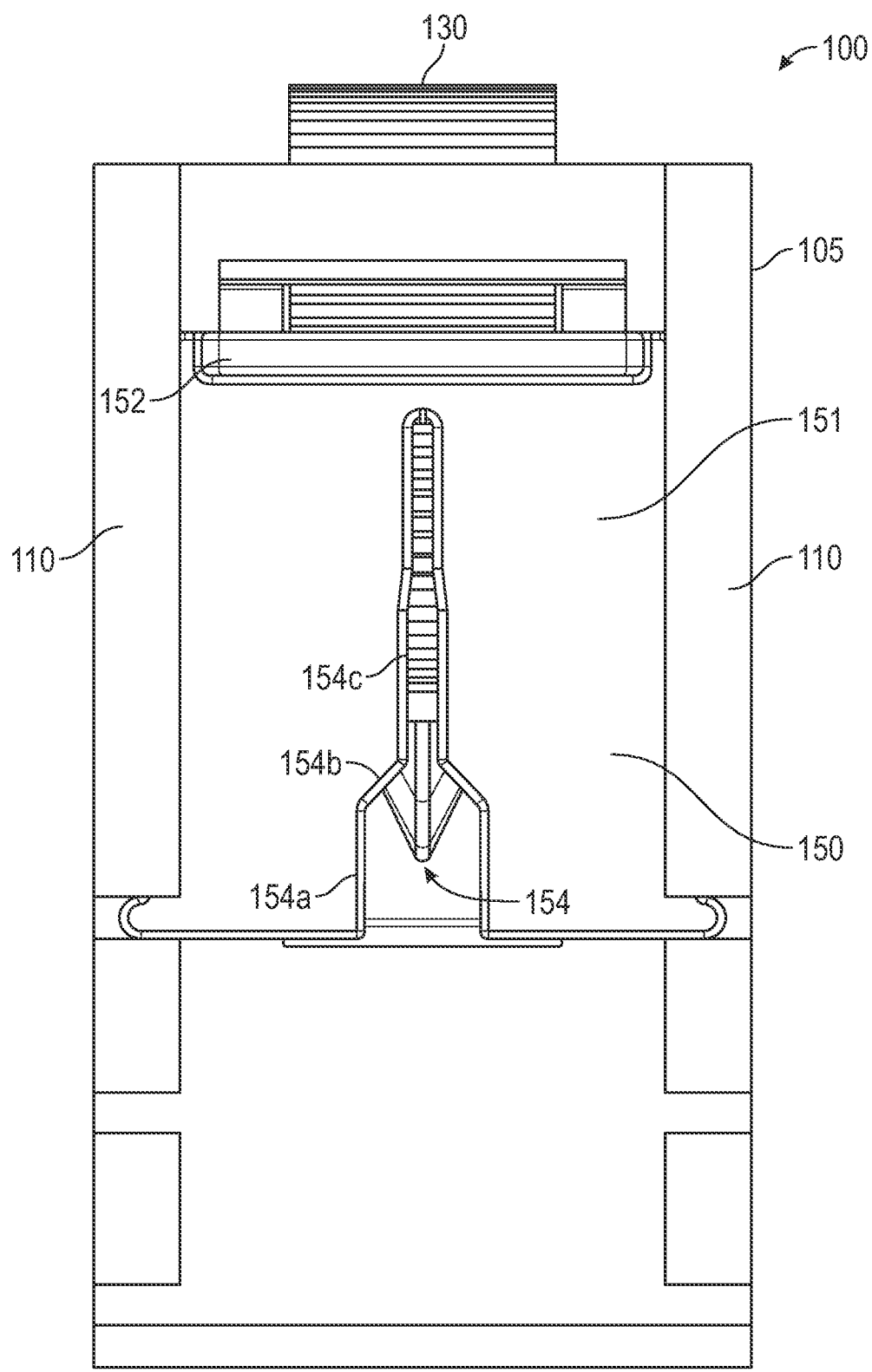
FIG. 5 depicts a front elevation view of the precision roller clamp assembly of FIG. 3.
Figure 6:
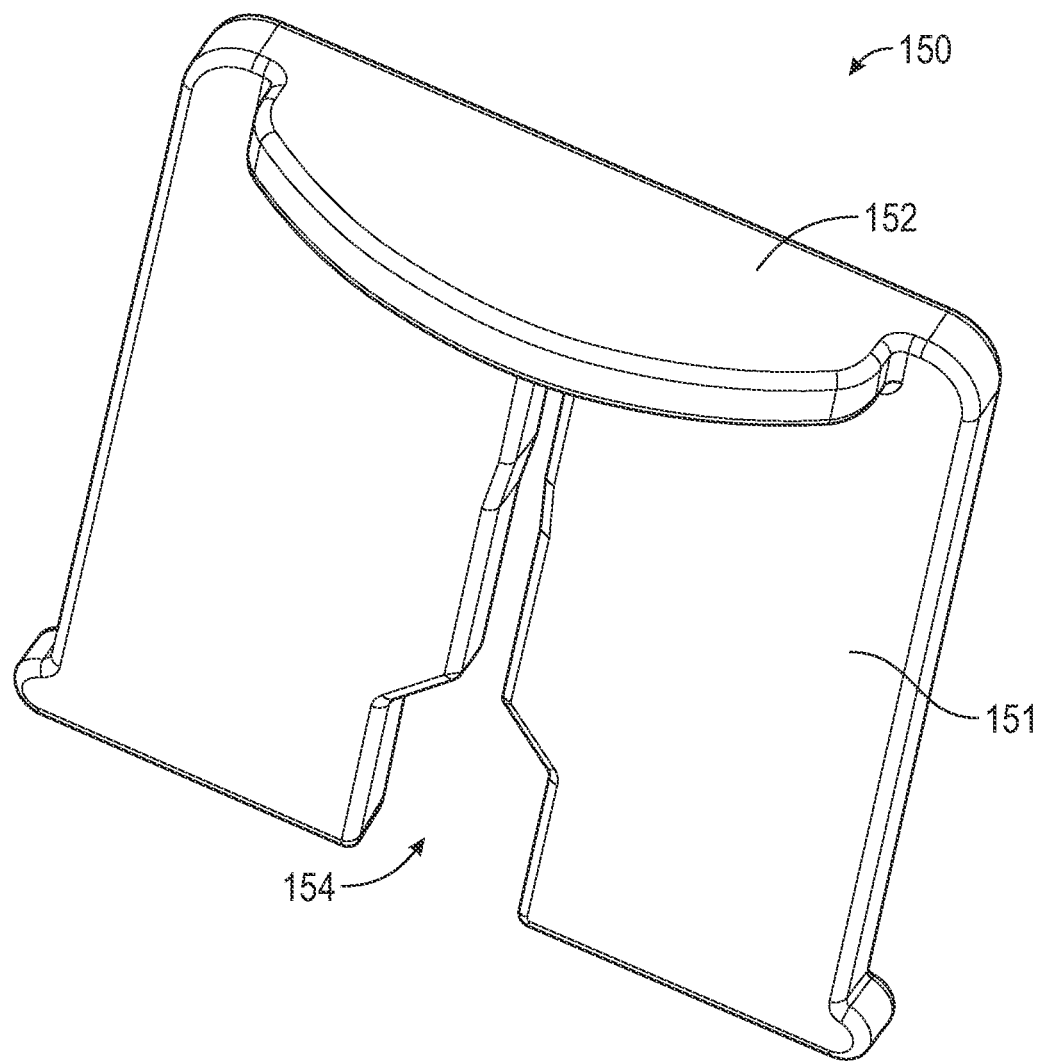
FIG. 6 depicts a perspective view of a slide plate from the precision roller clamp assembly of FIG. 3.
Figure 7:
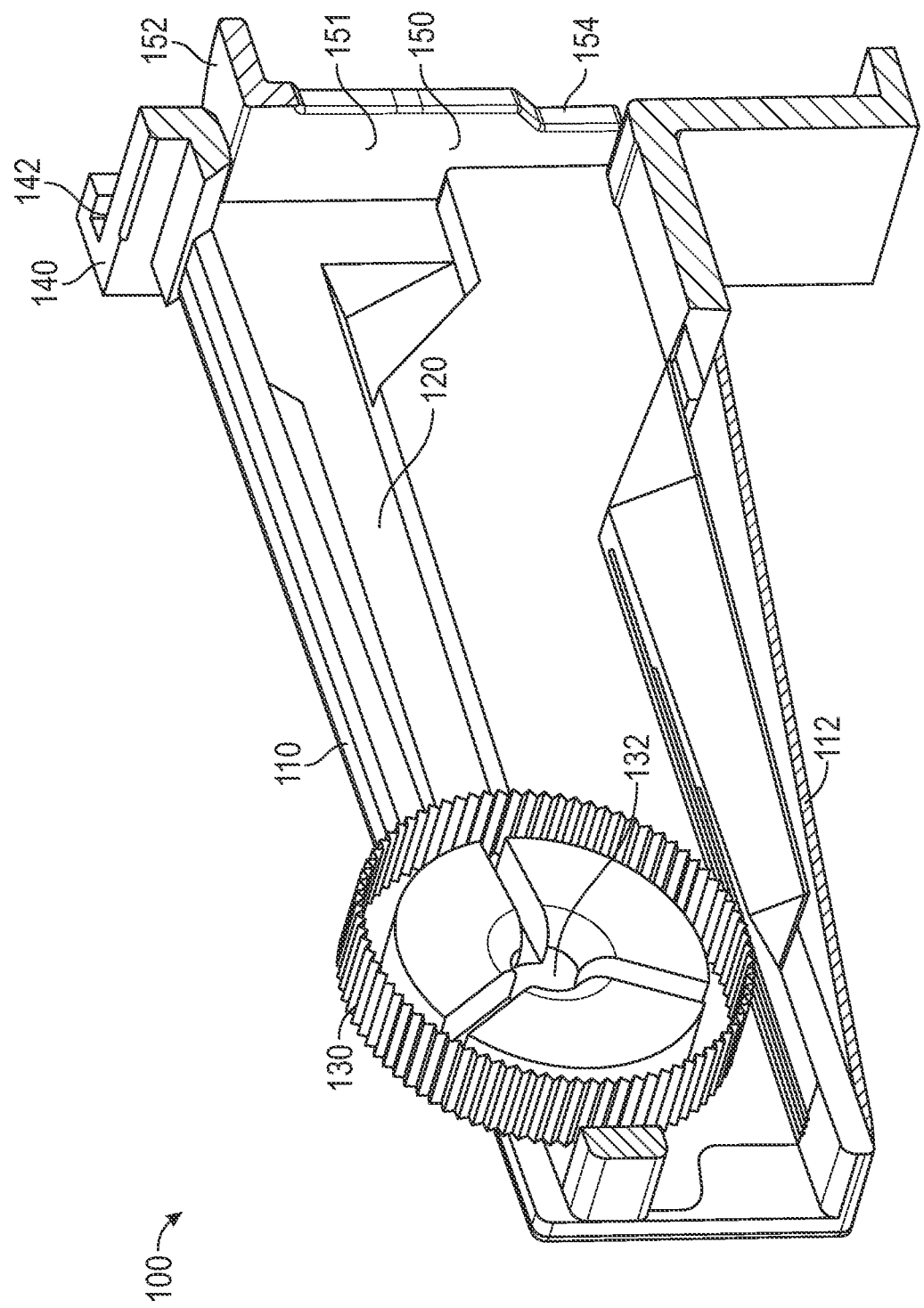
FIG. 7 depicts a cross-section perspective view of the precision roller clamp assembly of FIG. 3.

The tube engagement channel 154 may be configured to engage with the tube 24 and provide coarse control (e.g., rapid change) of the fluid flow rate through the tube 24. For example, as shown in FIGS. 5 and 6, the tube engagement channel 154 may have a first portion 154a having a uniform width, a second portion 154b having a linearly decreasing width, and a third portion 154c having a uniform width narrower than the width of the first portion. The different widths of the first, second and third portions 154a, 154b, 154c, allows the tube engagement channel 154 to engage with tube 24 of various sizes (e.g., diameters), for example. As another example, the different widths of the first, second and third portions 154a, 154b, 154c, allows the tube engagement channel 154 to provide different levels of compression or impingement on the same sized tube 24 based on how fare the slide plate 150 is moved towards the tube 24. The tube engagement channel 154 may be disposed centrally in a leading edge 156 of the slide plate 150, and the tube engagement channel 154 may have a steeple shape, as shown in FIG. 5.

For example, the slide plate 150 may be moved from a wide open position (e.g., not impinging upon tube 24) to an engaged position in which the tube 24 is engaged within the tube engagement channel 154. Thus, the slide plate 150 provides a coarse control where the fluid flow rate of 2,000 to 8,000 ml/hr in the wide open position may be quickly adjusted to a fluid flow rate of 250 ml/hr when the slide plate 150 is moved into the engaged position. As another example, the fluid flow rate may be quickly adjusted to a fully blocked flow rate of 0 ml/hr (e.g., quick occlusion), or any other desired fluid flow rate between 250 ml/hr and 0 ml/hr (e.g., 50 ml/hr, 125 ml/hr), when the slide plate 150 is moved into the fully engaged position. Thus, the slide plate 150 may be configured as a substantially binary flow switch (e.g., on/off switch), for example, where the flow rate is either wide open or adjusted down to a specific flow rate such as 250 ml/hr, or even to a fully blocked flow rate of 0 ml/hr.

The combination of the slide plate 150 and the roller 130 provides for both coarse and fine control of the fluid flow in tube 24. For example, with both the slide plate 150 and the roller 130 in their respective wide open positions, the slide plate 150 may be moved to the engaged position, thus quickly adjusting the fluid flow rate of 2,000 to 8,000 ml/hr down to 250 ml/hr, or even to a fully blocked flow (e.g., quick occlusion). For an adjusted fluid flow rate that is not fully occluded, the roller 130 may then be moved within the housing 105 to increasingly impinge further upon tube 24 in a more gradual manner, providing a finer and more precise adjustment of the fluid flow rate. For example, the roller 130 may be moved from its wide open position near one end of the housing 105 in which the fluid flow rate is 250 ml/hr to a fully impinging position towards the opposite end of the housing 105 in which the fluid flow rate is 0 ml/hr (e.g., fully blocked). The length of travel of the roller 130 between the two positions allows for granular and precise changes in fluid flow rate via the roller 130 with the slide plate 150 engaged. For an adjusted fluid flow rate that is fully occluded after full engagement of the slide plate 150, movement of the roller 130 may not be needed nor provide further flow rate adjustment.

The precision roller clamp assembly 100 may be configured so that the slide plate 150 is automatically moved to the fully engaged position when the roller 130 is moved from its wide open position to an initial control position (e.g., where the roller 130 initially begins to impinge the tube 24). In this manner, a user (e.g., healthcare provider, patient) or an adjustment device only needs to touch and adjust the roller 130.

Figure 8:
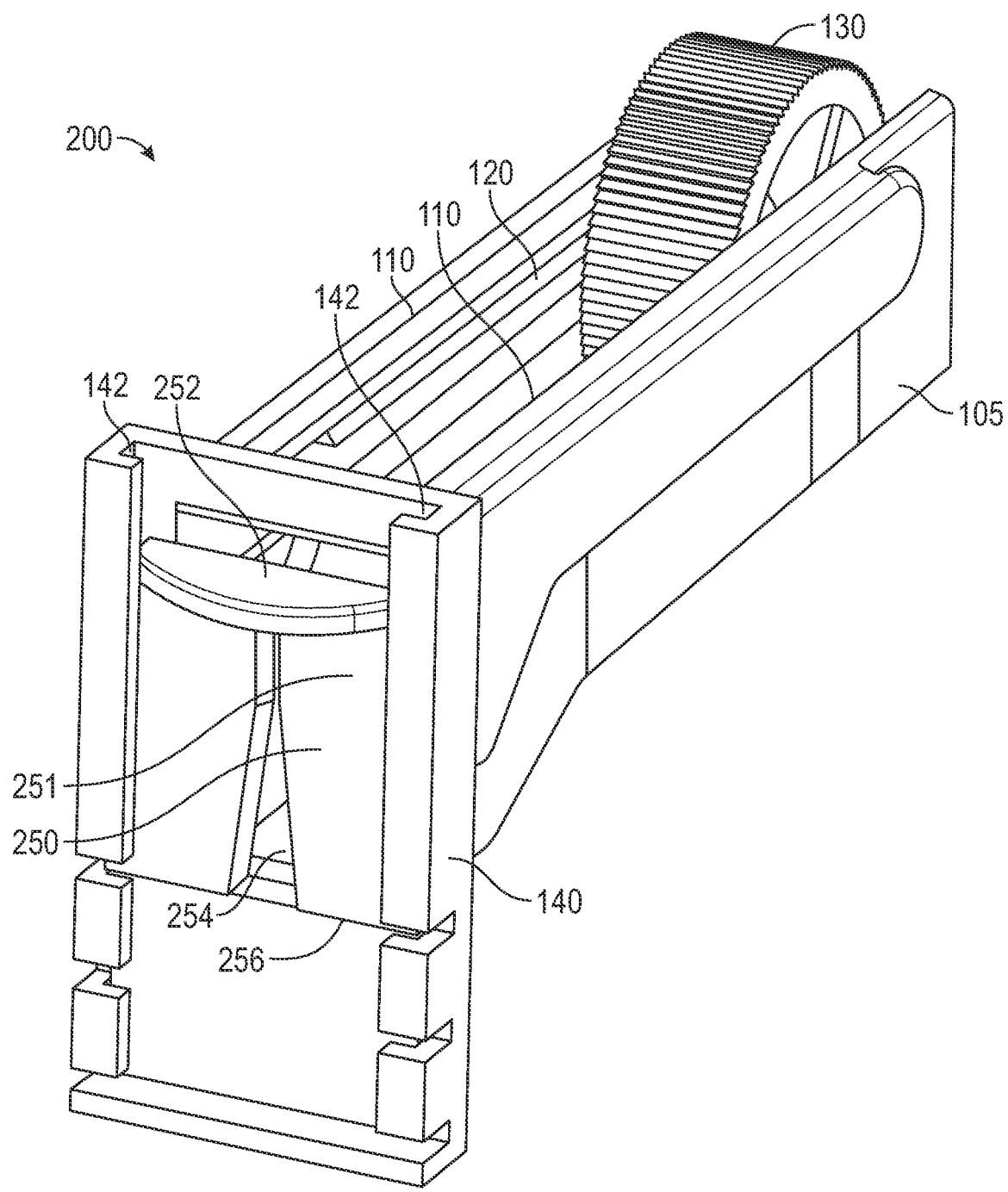
FIG. 8 depicts a perspective view of a precision roller clamp assembly.
Figure 9:
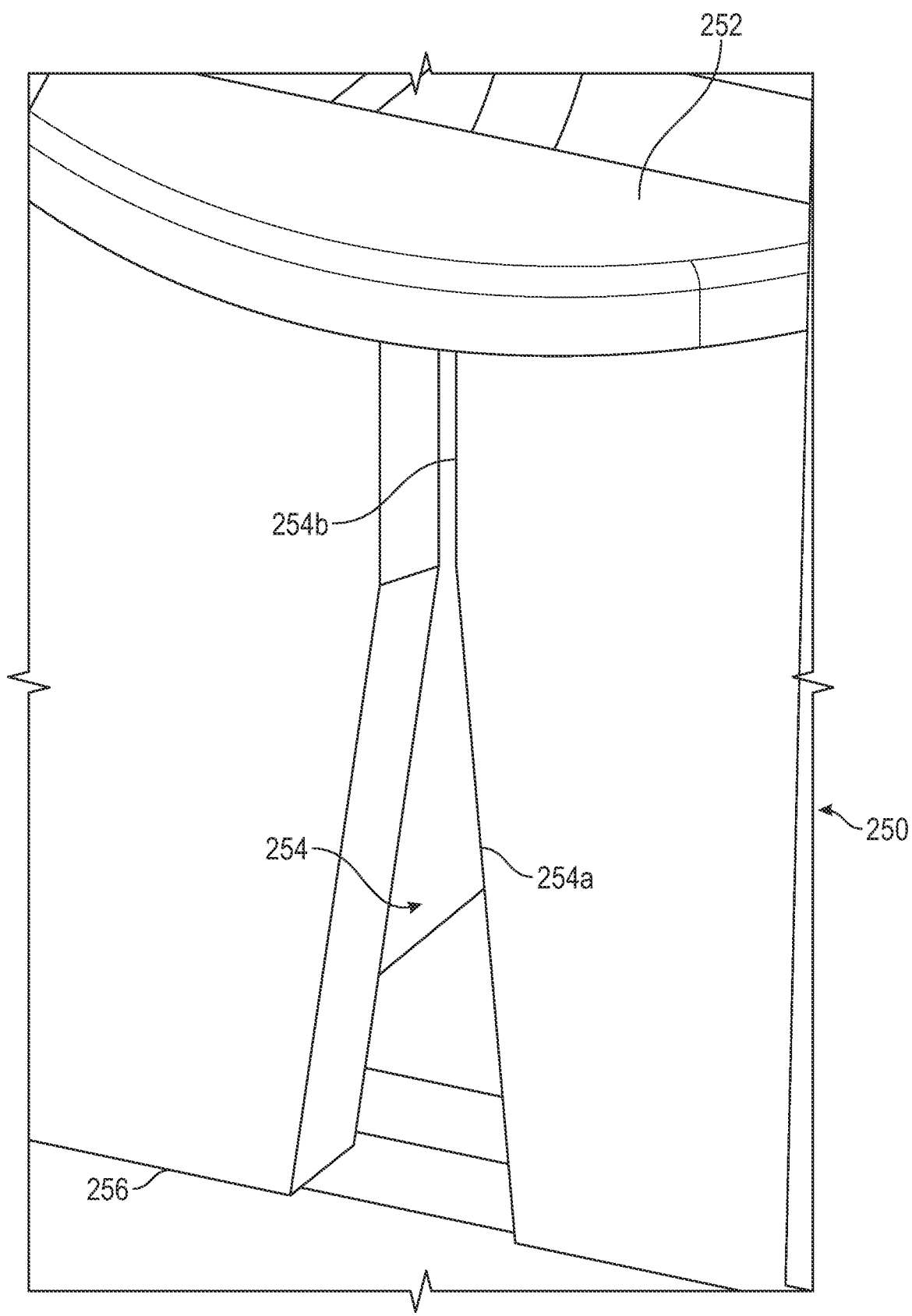
FIG. 9 depicts a perspective view of a slide plate from the precision roller clamp assembly of FIG. 8.

With reference to FIGS. 8 and 9, a multistage precision roller clamp assembly 200 is shown. Many of the features of roller clamp assembly 200 are the same as that of roller clamp assembly 100 and the same reference numbers are used for those features. The roller clamp assembly 200 has a housing 105 having an open-ended boxlike construction and is dimensioned and configured to receive tubing, such as connector tube 24. Two opposing side walls 110 each have a guide groove 120 that are aligned with each other and face each other. A flow-regulating roller 130 is provided having axially-projecting shafts 132 protruding from the centers of each side of the roller 130. The shafts 132 of the roller 130 are seated in the guide grooves 120 so that the roller 130 can move up and down the guide grooves 120. A guide wall 112 is opposed to the roller 130 and the surface of the guide wall 112 converges along its length toward the position of the guide grooves 120.

The roller clamp assembly 200 also includes a front wall 140 disposed at one end of the side walls 110. The front wall 140 includes grooves 142 configured to receive a slide plate 250. The slide plate 250 includes a plate wall 251, a grip member 252 and a tube engagement channel 254. The grip member 252 may protrude out (e.g., project orthogonally) from the plate wall 251 and provide a surface that may be pushed or pulled to slidably move the slide plate 250 within the grooves 142, the slide plate 250 being movable towards or away from the tube 24 disposed through the roller clamp assembly 200.

The tube engagement channel 254 may be configured to engage with the tube 24 and provide coarse control (e.g., rapid change) of the fluid flow rate through the tube 24. For example, as shown in FIG. 9, the tube engagement channel

254 may have a first portion 254a having a linearly decreasing width and a second portion 254b having a uniform width. The varying width of the first portion 254a allows the tube engagement channel 254 to engage with tube 24 of various sizes (e.g., diameters), for example. As another example, the varying width of the first portion 254a allows the tube engagement channel 254 to provide different levels of compression or impingement on the same sized tube 24 based on how far the slide plate 250 is moved towards the tube 24. The tube engagement channel 254 may be disposed centrally in the slide plate 250 and linearly narrow inwards from a leading edge 256 of the slide plate 250. Thus, the tube engagement channel 254 may have a substantially triangular shape, as shown in FIG. 9.

For example, the slide plate 250 may be moved from a wide open position (e.g., not impinging upon tube 24) to an initial engaged position in which the tube 24 is initially engaged but not impinged by the tube engagement channel 254. From the initial engaged position, the slide plate 250 may be moved further towards the tube 24 such that the tube 24 is engaged by narrower portions of the tube engagement channel 254, which impinges the tube 24 to a greater degree and causes a reduction in the fluid flow rate. The slide plate 250 may have a fully engaged position in which the tube 24 is engaged by narrow most portions of the tube engagement channel 254. Thus, the slide plate 250 provides a coarse control where, for example, the fluid flow rate of 2,000 to 8,000 ml/hr in the wide open position may be quickly adjusted to a fluid flow rate of 250 ml/hr when the slide plate 250 is moved into the fully engaged position. As another example, the fluid flow rate may be quickly adjusted to a fully blocked flow rate of 0 ml/hr (e.g., quick occlusion), or any other desired fluid flow rate between 250 ml/hr and 0 ml/hr (e.g., 50 ml/hr, 125 ml/hr), when the slide plate 250 is moved into the fully engaged position. Positioning the slide plate 250 between the wide open position and the fully engaged position will result in the fluid flow rate being between the wide open rate and the fully engaged rate. Thus, the slide plate 250 may be configured as a linearly adjusting flow switch (e.g., dimmer switch), for example, where the flow rate linearly adjusts down from a wide open flow rate to a final coarse flow rate (e.g., 250 ml/hr), or even to a fully blocked flow rate (e.g., 0 ml/hr).

The combination of the slide plate 250 and the roller 130 provides for both coarse and fine control of the fluid flow in tube 24. For example, with both the slide plate 250 and the roller 130 in their respective wide open positions, the slide plate 250 may be moved towards or to the fully engaged position, thus quickly adjusting the fluid flow rate anywhere from the wide open rate of 2,000 to 8,000 ml/hr down to 250 ml/hr, or even to a fully blocked flow (e.g., quick occlusion). For an adjusted fluid flow rate that is not fully occluded, the roller 130 may then be moved within the housing 105 to increasingly impinge further upon tube 24 in a more gradual manner, providing a finer and more precise adjustment of the fluid flow rate. For example, the roller 130 may be moved from its wide open position near one end of the housing 105 in which the fluid flow rate is 250 ml/hr to a fully impinging position towards the opposite end of the housing 105 in which the fluid flow rate is 0 ml/hr (e.g., fully blocked). The length of travel of the roller 130 between the two positions allows for granular and precise changes in fluid flow rate via the roller 130 with the slide plate 250 partially or fully engaged. For an adjusted fluid flow rate that is fully occluded after full engagement of the slide plate 250, movement of the roller 130 may not be needed nor provide further flow rate adjustment.

The precision roller clamp assembly 200 may be configured so that the slide plate 250 is automatically moved to a particular engaged position when the roller 130 is moved from its wide open position to an initial control position (e.g., where the roller 130 initially begins to impinge the tube 24). In this manner, a user (e.g., healthcare provider, patient) or an adjustment device only needs to touch and adjust the roller 130.

Figure 10:
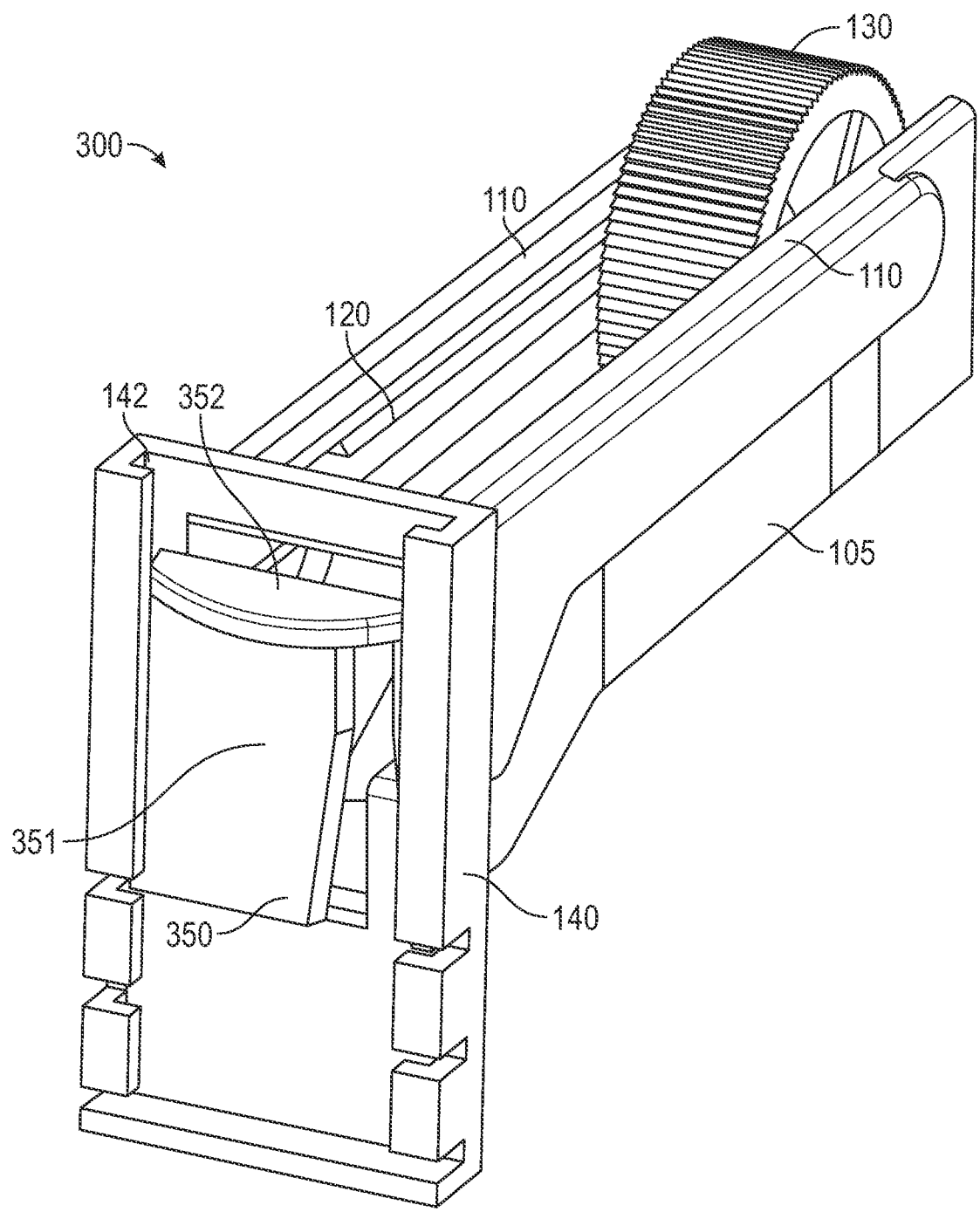
FIG. 10 depicts a perspective view of a precision roller clamp assembly.
Figure 11:
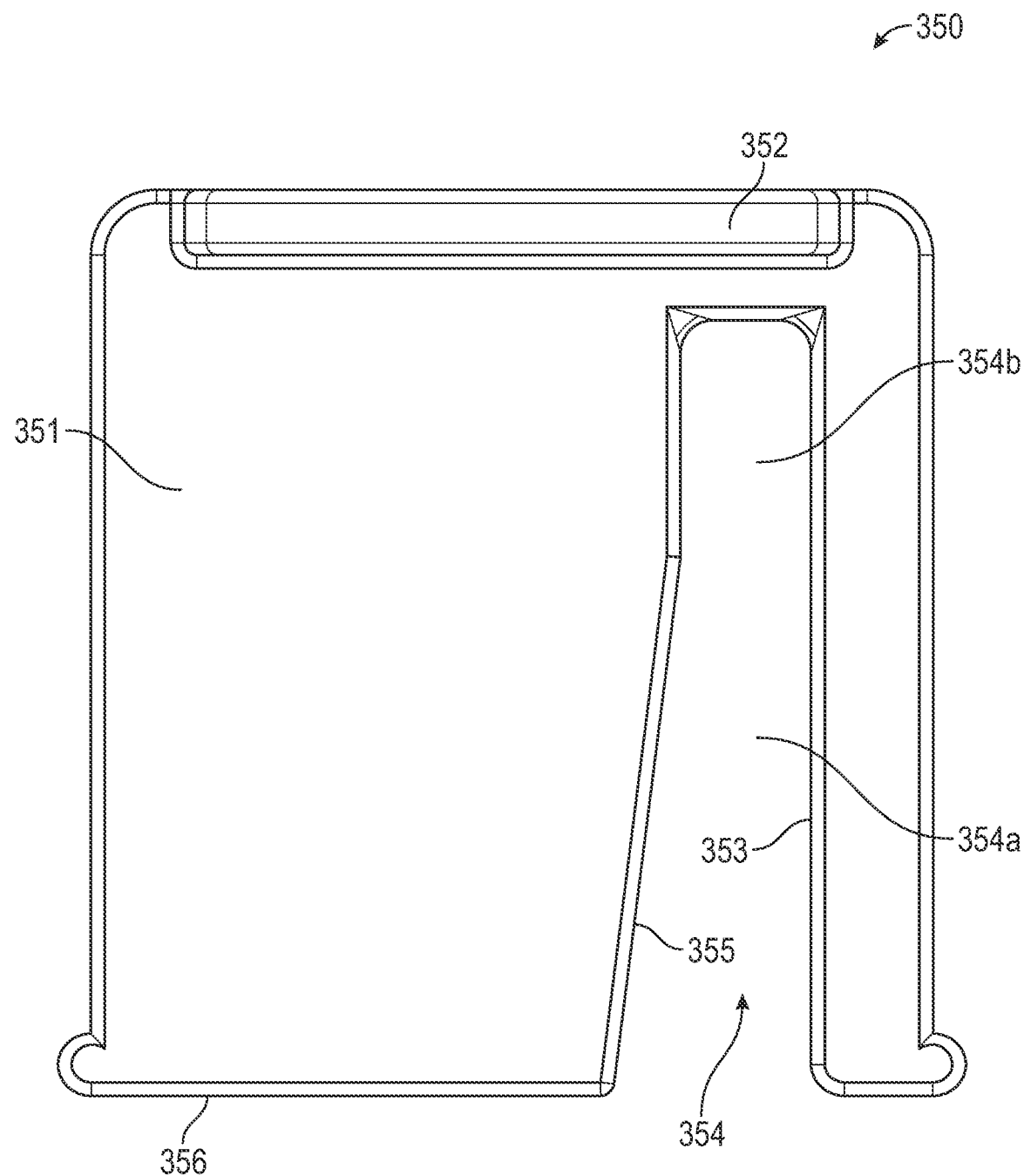
FIG. 11 depicts a perspective view of a slide plate from the precision roller clamp assembly of FIG. 10.
Figure 12:
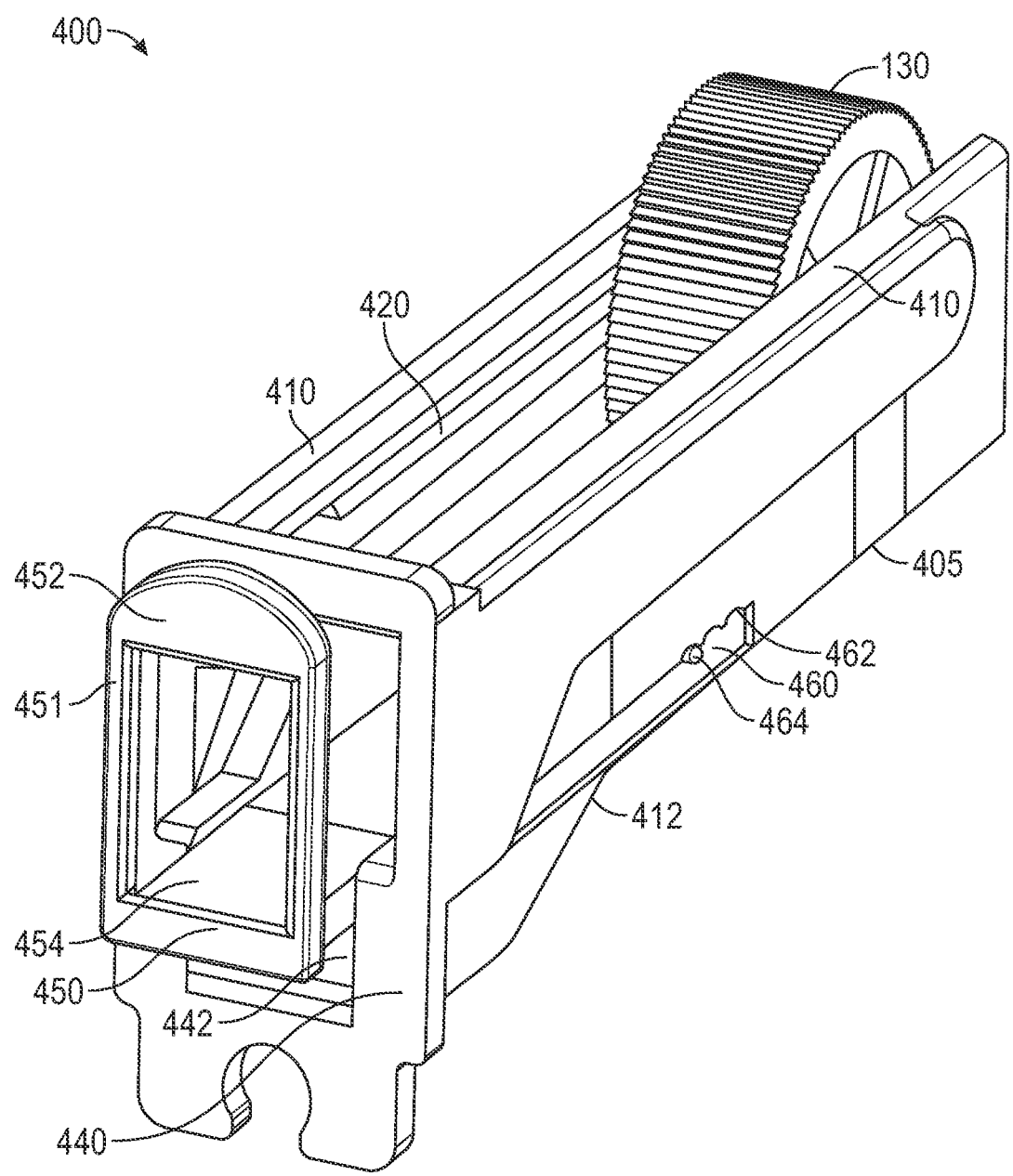
FIG. 12 depicts a perspective view of a precision roller clamp assembly.
Figure 13:
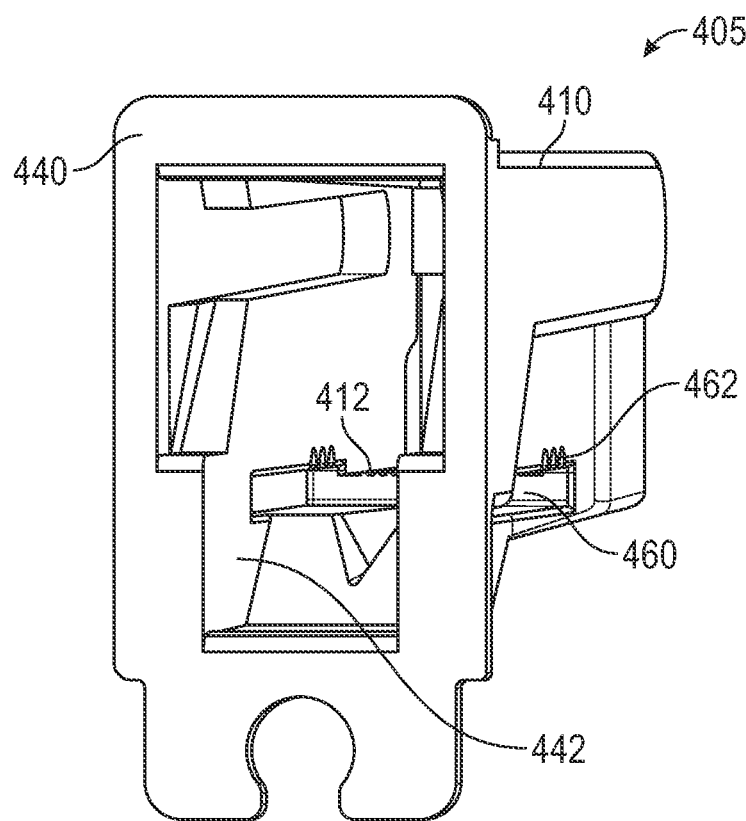
FIG. 13 depicts a perspective view of a housing of the precision roller clamp assembly of FIG. 12.
Figure 14:
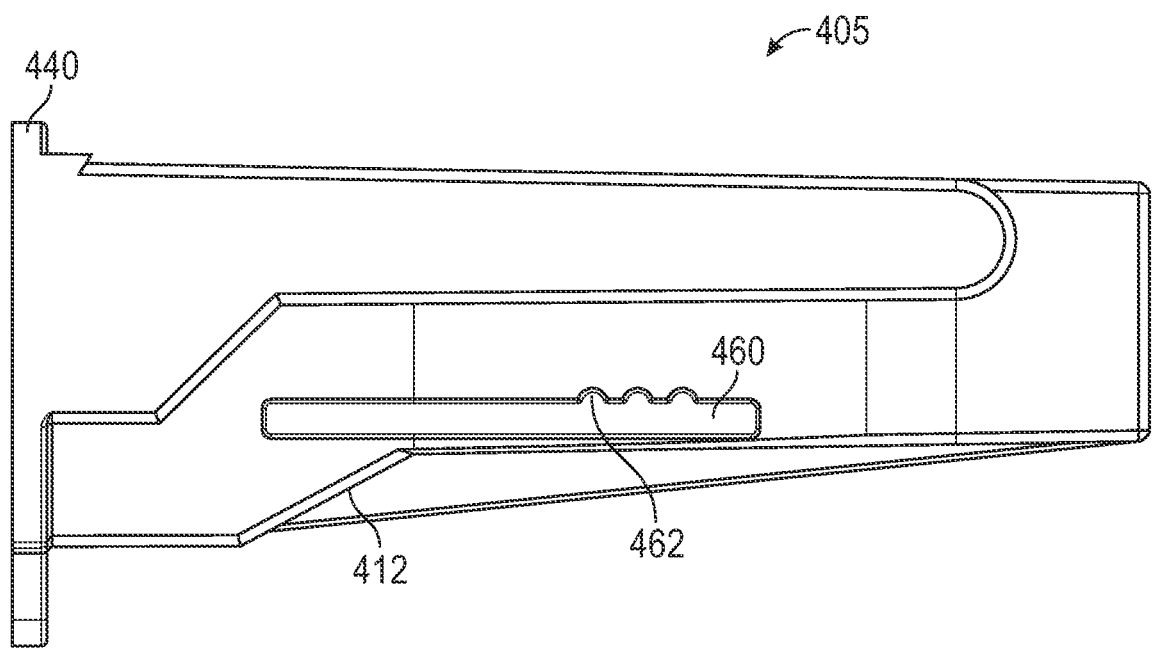
FIG. 14 depicts a side view of the housing of FIG. 13.
Figure 15:
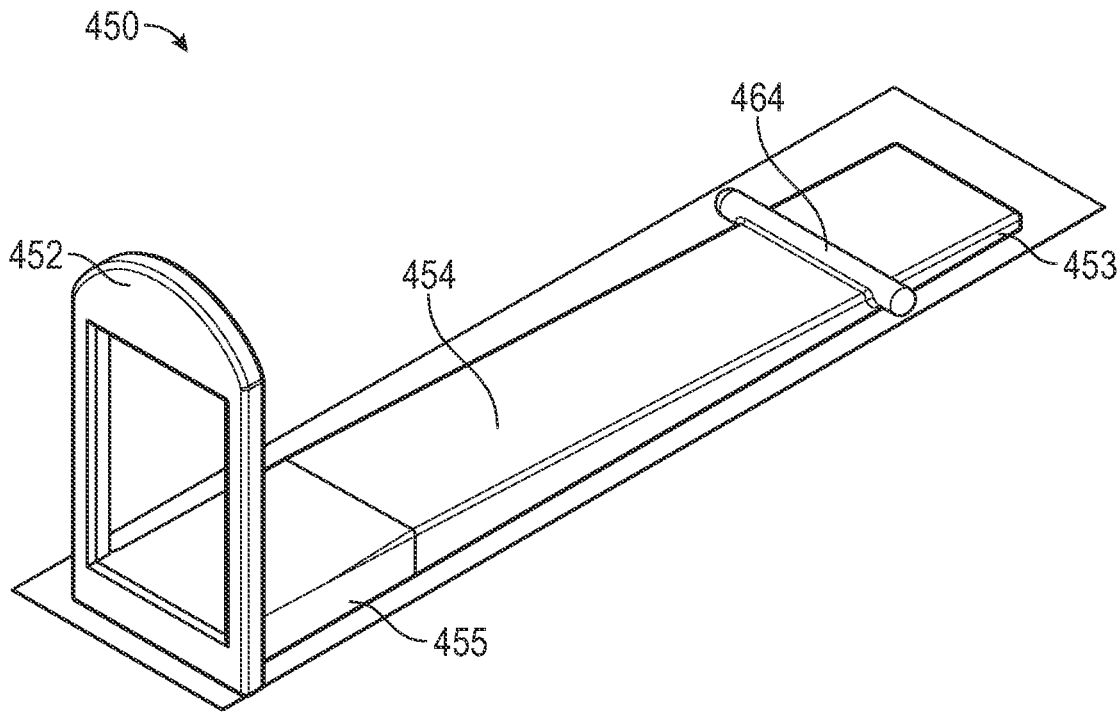
FIG. 15 depicts a perspective view of a shim plate of the precision roller clamp assembly of FIG. 12.

With reference to FIGS. 10 and 11, a multistage precision roller clamp assembly 300 is shown. Many of the features of roller clamp assembly 300 are the same as that of roller clamp assembly 100 and the same reference numbers are used for those features. The roller clamp assembly 300 has a housing 105 having an open-ended boxlike construction and is dimensioned and configured to receive tubing, such as connector tube 24. Two opposing side walls 110 each have a guide groove 120 that are aligned with each other and face each other. A flow-regulating roller 130 is provided having axially-projecting shafts 132 protruding from the centers of each side of the roller 130. The shafts 132 of the roller 130 are seated in the guide grooves 120 so that the roller 130 can move up and down the guide grooves 120. A guide wall 112 is opposed to the roller 130 and the surface of the guide wall 112 converges along its length toward the position of the guide grooves 120.

The roller clamp assembly 300 also includes a front wall 140 disposed at one end of the side walls 110. The front wall 140 includes grooves 142 configured to receive a slide plate 350. The slide plate 350 includes a plate wall 351, a grip member 352 and a tube engagement channel 354. The grip member 352 may protrude out (e.g., project orthogonally) from the plate wall 351 and provide a surface that may be pushed or pulled to slidably move the slide plate 350 within the grooves 142, the slide plate 350 being movable towards or away from the tube 24 disposed through the roller clamp assembly 300.

The tube engagement channel 354 may be configured to engage with the tube 24 and provide coarse control (e.g., rapid change) of the fluid flow rate through the tube 24. For example, as shown in FIG. 11, the tube engagement channel 354 may have a first portion 354a having a linearly decreasing width and a second portion 354b having a uniform width. The varying width of the first portion 354a allows the tube engagement channel 354 to engage with tube 24 of various sizes (e.g., diameters), for example. As another example, the varying width of the first portion 354a allows the tube engagement channel 354 to provide different levels of compression or impingement on the same sized tube 24 based on how far the slide plate 350 is moved towards the tube 24. The tube engagement channel 354 may be disposed offset to the center of the slide plate 350 (e.g., towards one side). The tube engagement channel 354 may have one straight side 353 and another angled side 355 having a portion that linearly narrows inwards from a leading edge 356 of the slide plate 350. Thus, the tube engagement channel 354 may have a melded rectangular/angular shape, as shown in FIG. 11.

For example, the slide plate 350 may be moved from a wide open position (e.g., not impinging upon tube 24) to an initial engaged position in which the tube 24 is initially engaged but not impinged by the tube engagement channel 354. From the initial engaged position, the slide plate 350 may be moved further towards the tube 24 such that the tube 24 is engaged by narrower portions of the tube engagement channel 354, which impinges the tube 24 to a greater degree and causes a reduction in the fluid flow rate. The slide plate 350 may have a fully engaged position in which the tube 24 is engaged by narrow most portions of the tube engagement channel 354. Thus, the slide plate 350 provides a coarse control where, for example, the fluid flow rate of 2,000 to 8,000 ml/hr in the wide open position may be quickly adjusted to a fluid flow rate of 250 ml/hr when the slide plate 350 is moved into the fully engaged position. As another example, the fluid flow rate may be quickly adjusted to a fully blocked flow rate of 0 ml/hr (e.g., quick occlusion), or any other desired fluid flow rate between 250 ml/hr and 0 ml/hr (e.g., 50 ml/hr, 125 ml/hr), when the slide plate 350 is moved into the fully engaged position. Positioning the slide plate 350 between the wide open position and the fully engaged position will result in the fluid flow rate being between the wide open rate and the fully engaged rate. Thus, the slide plate 350 may be configured as a linearly adjusting flow switch (e.g., dimmer switch), for example, where the flow rate linearly adjusts down from a wide open flow rate to a final coarse flow rate (e.g., 250 ml/hr), or even to a fully blocked flow rate (e.g., 0 ml/hr).

The combination of the slide plate 350 and the roller 130 provides for both coarse and fine control of the fluid flow in tube 24. For example, with both the slide plate 350 and the roller 130 in their respective wide open positions, the slide plate 350 may be moved towards or to the fully engaged position, thus quickly adjusting the fluid flow rate anywhere from the wide open rate of 2,000 to 8,000 ml/hr down to 250 ml/hr, or even to a fully blocked flow (e.g., quick occlusion). For an adjusted fluid flow rate that is not fully occluded, the roller 130 may then be moved within the housing 105 to increasingly impinge further upon tube 24 in a more gradual manner, providing a finer and more precise adjustment of the fluid flow rate. For example, the roller 130 may be moved from its wide open position near one end of the housing 105 in which the fluid flow rate is 250 ml/hr to a fully impinging position towards the opposite end of the housing 105 in which the fluid flow rate is 0 ml/hr (e.g., fully blocked). The length of travel of the roller 130 between the two positions allows for granular and precise changes in fluid flow rate via the roller 130 with the slide plate 350 partially or fully engaged. For an adjusted fluid flow rate that is fully occluded after full engagement of the slide plate 350, movement of the roller 130 may not be needed nor provide further flow rate adjustment.

The precision roller clamp assembly 300 may be configured so that the slide plate 350 is automatically moved to a particular engaged position when the roller 130 is moved from its wide open position to an initial control position (e.g., where the roller 130 initially begins to impinge the tube 24). In this manner, a user (e.g., healthcare provider, patient) or an adjustment device only needs to touch and adjust the roller 130.

With reference to FIGS. 12-15, a multistage precision roller clamp assembly 400 is shown. Some of the features of roller clamp assembly 400 are the same as that of roller clamp assembly 100 and the same reference numbers are used for those features. The roller clamp assembly 400 has a housing 405 having an open-ended boxlike construction and is dimensioned and configured to receive tubing, such as connector tube 24. Two opposing side walls 410 each have a guide groove 420 that are aligned with each other and face each other. A flow-regulating roller 130 is provided having axially-projecting shafts 132 protruding from the centers of each side of the roller 130. The shafts 132 of the roller 130 are seated in the guide grooves 420 so that the roller 130 can move up and down the guide grooves 420. A guide wall 412 is opposed to the roller 130 and the surface of the guide wall 412 converges along its length toward the position of the guide grooves 420.

The roller clamp assembly 400 also includes a front wall 440 disposed at one end of the side walls 410. The front wall 440 includes an opening 442 configured to receive a shim plate 450. The shim plate 450 includes a plate wall 451, a grip member 452 and a tube engagement wall 454. The grip member 452 may extend out (e.g., project linearly) from the plate wall 451 and provide a surface that may be pushed or pulled to slidably move the shim plate 450 back and forth within the housing 405. The shim plate 450 is movable in parallel with the tube 24 disposed through the roller clamp assembly 400, so that the thickness of the tube engagement wall 454 may vary at a particular portion of the tube 24. For example, the tube engagement wall 454 may have a varying thickness with a thinnest portion 453 at one end and a thickest portion 455 at the other end (e.g., a shim). The tube engagement wall 454 may be configured to engage with the tube 24 and provide coarse control (e.g., rapid change) of the fluid flow rate through the tube 24.

For example, the shim plate 450 may be moved from a wide open position in which the thinnest portion 453 of the tube engagement wall 454 may be engaged with but not impinging upon tube 24, to an engaged position in which the thickest portion 455 of the tube engagement wall 454 is engaged with and impinging the tube 24. Thus, the shim plate 450 provides a coarse control where the fluid flow rate of 2,000 to 8,000 ml/hr in the wide open position may be quickly adjusted to a fluid flow rate of 250 ml/hr when the shim plate 450 is moved into the engaged position. As another example, the fluid flow rate may be quickly adjusted to a fully blocked flow rate of 0 ml/hr (e.g., quick occlusion), or any other desired fluid flow rate between 250 ml/hr and 0 ml/hr (e.g., 50 ml/hr, 125 ml/hr), when the shim plate 450 is moved into the fully engaged position. Thus, the shim plate 450 may be configured as a linearly adjusting flow switch (e.g., dimmer switch), for example, where the flow rate linearly adjusts down from a wide open flow rate to a final coarse flow rate (e.g., 250 ml/hr), or even to a fully blocked flow rate (e.g., 0 ml/hr).

The combination of the shim plate 450 and the roller 130 provides for both coarse and fine control of the fluid flow in tube 24. For example, with both the shim plate 450 and the roller 130 in their respective wide open positions, the shim plate 450 may be moved towards or to the fully engaged position, thus quickly adjusting the fluid flow rate anywhere from the wide open rate of 2,000 to 8,000 ml/hr down to 250 ml/hr, or even to a fully blocked flow (e.g., quick occlusion). For an adjusted fluid flow rate that is not fully occluded, the roller 130 may then be moved within the housing 405 to increasingly impinge further upon tube 24 in a more gradual manner, providing a finer and more precise adjustment of the fluid flow rate. For example, the roller 130 may be moved from its wide open position near one end of the housing 405 in which the fluid flow rate is 250 ml/hr to a fully impinging position towards the opposite end of the housing 405 in which the fluid flow rate is 0 ml/hr (e.g., fully blocked). The length of travel of the roller 130 between the two positions allows for granular and precise changes in fluid flow rate via the roller 130 with the shim plate 450 partially or fully engaged. For an adjusted fluid flow rate that is fully occluded after full engagement of the shim plate 450, movement of the roller 130 may not be needed nor provide further flow rate adjustment.

The precision roller clamp assembly 400 may be configured so that the shim plate 450 is automatically moved to a particular engaged position when the roller 130 is moved from its wide open position to an initial control position (e.g., where the roller 130 initially begins to impinge the tube 24). In this manner, a user (e.g., healthcare provider, patient) or an adjustment device only needs to touch and adjust the roller 130.

The housing 405 may include a guide channel 460 disposed within each side wall 410. The guide channel 460 may have one or more retention sections 462 configured to receive a retention pin 464 coupled to the tube engagement wall 454. For example, when the retention pin 464 is disposed within an opposing pair of retention sections 462, the shim plate 450 may be held in place within the housing 405. A pushing or pulling force on the grip member 452 may overcome the retention force of the retention pin 464 engaged with the retention sections 462, allowing the tube engagement wall 454 to move further into or out of the housing 405. Also, the shim plate 450 may be configured, via the angle of the shim plate 450 and the retention sections 462, to prevent slippage of the roller 130 in order to minimize or prevent flow rate drifting. Accordingly, the roller 130 may only slip forwards to further close the clamping gap, but may be prevented from slipping backwards, thus preventing further opening the clamping gap.

Figure 16:
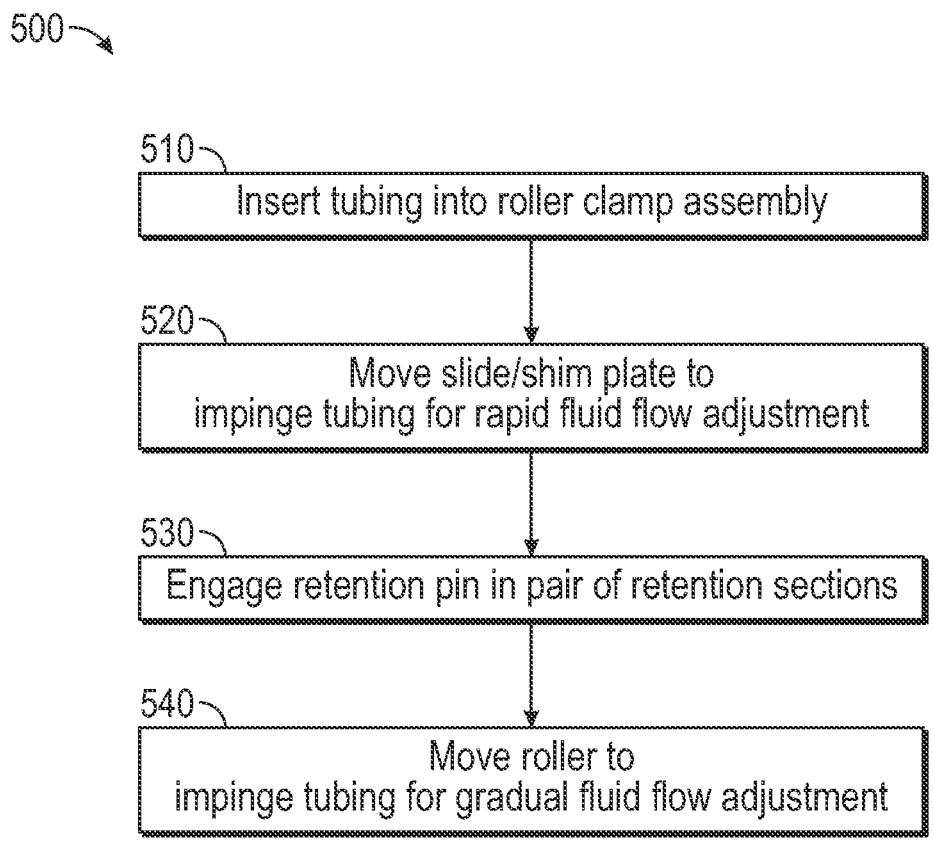
FIG. 16 depicts a method of using a precision roller clamp assembly.

With reference to FIG. 16, a method 500 of operating a precision roller clamp assembly is provided. In step 510, tubing (e.g., IV tubing) is placed or disposed in a precision roller clamp assembly 100, 200, 300, 400. For example, tube 24 may be inserted into housing 105, 205, 305, 405 with both a slide/shim plate 150, 250, 350, 450 and a roller 130 in wide open positions (e.g., not contacting or impinging the tube 24).

The slide/shim plate 150, 250, 350, 450 is moved to engage and impinge the tube 24 in step 520. For example, the slide plate 150, 250, 350 may be moved on a front wall 140 end of the housing 105, 205, 305 orthogonally to and towards the tube 24 to cause a compression force to squeeze the contacted portion of the tube 24, thus causing the fluid flow rate in the tube 24 to rapidly change to a lower flow rate (e.g., from a wide open rate of 2,000 to 8,000 ml/hr down to 250 ml/hr, or even to a fully blocked flow or quick occlusion). As another example, the shim plate 450 may be moved further into the housing 405 in parallel with the tube 24, causing a compression force to squeeze the contacted portion of the tube 24 and causing the fluid flow rate in the tube 24 to rapidly change to a lower flow rate. With the use of the shim plate 450, the shim plate 450 is moved so that a retention pin 464 is received by a pair of retention sections 462 disposed in side walls 410 of the housing 405, in step 530.

In step 540, the roller 130 may be moved to engage and impinge the tube 24. For example, the roller 130 may be moved from the front wall 140, 440 end of the housing 105, 205, 305, 405 towards the opposite end of the housing 105, 205, 305, 405 so that a narrowing between a guide wall 112, 412 and the roller 130 causes the roller to compress or squeeze the contacted portion of the tube 24, thus causing the fluid flow rate in the tube 24 to slowly change to a lower or blocked flow rate (e.g., from 250 ml/hr to 0 ml/hr).

The slide/shim plate 150, 250, 350, 450 and the roller 130 may be adjusted independently to each other or in combination with each other to achieve the desired fluid flow rate in the tube 24. For example, one of the slide/shim plate 150, 250, 350, 450 and the roller 130 may be adjusted to impinge upon the tube 24 while the other of the slide/shim plate 150, 250, 350, 450 and the roller 130 remain in the wide open position. As another example, adjustment of the roller 130 may automatically adjust the slide/shim plate 150, 250, 350, 450. Thus, any combination of coarse and fine adjustments may be made to the fluid flow rate in the tube 24.

It is understood that any specific order or hierarchy of blocks in the methods of processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A roller clamp assembly comprising:
   a housing configured to receive a flexible tube, the housing comprising:
      two opposing side walls;
      a front wall disposed at one end of the side walls; and
      a guide wall disposed between the side walls;
   a roller wheel movably disposed in the housing, the roller wheel configured to move along a longitudinal axis of the housing, wherein spacing between the guide wall and the roller wheel decreases over a length of the guide wall; and
   a plate configured to slideably engage with a portion of the housing, the plate comprising:
      a grip member; and
      a tube engagement member configured to compress the flexible tube a varying amount as the plate is moved in relation to the housing.

2. The roller clamp assembly of claim 1, wherein sliding of the roller wheel in a direction of lesser spacing between the guide wall and the roller wheel causes the roller wheel to impinge on the flexible tube to a gradually increasing extent, wherein the increased impingement of the roller wheel on the flexible tube is configured to reduce a fluid flow rate through the flexible tube.

3. The roller clamp assembly of claim 1, wherein the front wall comprises two grooves, each groove configured to slidingly receive a portion of the plate.

4. The roller clamp assembly of claim 1, wherein the tube engagement member is a channel centrally disposed on a leading edge of the plate.

5. The roller clamp assembly of claim 4, wherein the channel comprises a first portion having a first uniform width, a second portion having a varying width that decreases as a distance from the leading edge of the plate increases, and a third portion having a second uniform width that is less than the first uniform width.

6. The roller clamp assembly of claim 4, wherein the channel comprises a first portion having a varying width that decreases as a distance from the leading edge of the plate increases and a second portion having a uniform width.

7. The roller clamp assembly of claim 4, wherein at least a portion of the channel comprises a linearly decreasing width as a distance from the leading edge of the plate increases.

8. The roller clamp assembly of claim 1, wherein the tube engagement member is a channel disposed in an offset from central position on a leading edge of the plate.

9. The roller clamp assembly of claim 8, wherein the channel comprises a first portion having a varying width that decreases as a distance from the leading edge of the plate increases and a second portion having a uniform width.

10. The roller clamp assembly of claim 8, wherein the channel comprises a first straight side extending from the leading edge of the plate and a second opposing side having an angled portion extending from the leading edge of the plate.

11. The roller clamp assembly of claim 1, wherein the housing has an open-ended boxlike construction.

12. The roller clamp assembly of claim 1, wherein the plate is configured to provide a first amount of compression to the flexible tube and the roller wheel is configured to provide a second amount of compression to the flexible tube.

13. The roller clamp assembly of claim 12, wherein the first amount of compression comprises a rapid impingement to the flexible tube and the second amount of compression comprises a gradual impingement to the flexible tube.

14. The roller clamp assembly of claim 1, wherein each side wall comprises a guide channel disposed on a longitudinal axis of the housing, each guide channel having one or more retention sections.

15. The roller clamp assembly of claim 14, wherein the tube engagement member comprises an engagement wall having a varying thickness.

16. The roller clamp assembly of claim 15, further comprising a retention pin coupled to the engagement wall, the retention pin configured to be received by a pair of opposing retention sections.

17. The roller clamp assembly of claim 15, wherein the engagement wall is configured to be slidably moveable along the guide wall to provide a shim force on the flexible tube.

18. An infusion set comprising:
   an infusion component;
   a flexible tube; and
   a roller clamp assembly, the roller clamp assembly comprising:
      a housing configured to receive a flexible tube, the housing comprising:
         two opposing side walls;
         a front wall disposed at one end of the side walls; and
         a guide wall disposed between the side walls;
      a roller wheel movably disposed in the housing, the roller wheel configured to move along a longitudinal axis of the housing, wherein spacing between the guide wall and the roller wheel decreases over a length of the guide wall; and
      a plate configured to slideably engage with a portion of the housing, the plate comprising:
         a grip member; and
         a tube engagement member configured to compress the flexible tube a varying amount as the plate is moved in relation to the housing, wherein an increased impingement of the roller wheel on the flexible tube is configured to reduce a fluid flow rate through the flexible tube.

19. A method of adjusting a fluid flow rate through a flexible tube coupled to a fluid source, the method comprising:
   inserting the flexible tube through the housing of the roller clamp assembly of claim 1;
   sliding the plate relative to the housing to compress the flexible tubing with a first impingement to produce a coarse adjustment that causes a rapid decrease in the fluid flow rate through the flexible tube; and
   rolling the roller wheel relative to the housing to compress the flexible tubing with a second impingement to produce a fine adjustment that causes a further gradual decrease in the fluid flow rate through the flexible tube.

20. The method according to claim 19, wherein the sliding the plate comprises one of:
   sliding the plate in grooves on an exterior wall of the housing, wherein the plate moves orthogonally to the flexible tube; and
   sliding the plate along an interior wall of the housing, wherein the plate moves in parallel to the flexible tube.

* * * * *